United States Patent [19]

Gerberich et al.

[11] 4,420,641

[45] Dec. 13, 1983

[54] FORMALDEHYDE PRODUCTION

[75] Inventors: H. Robert Gerberich; Eldred T. Smith, both of Corpus Christi, Tex.

[73] Assignee: Celanese Corporation, New York, N.Y.

[21] Appl. No.: 457,335

[22] Filed: Jan. 12, 1983

Related U.S. Application Data

[62] Division of Ser. No. 287,385, Jul. 27, 1981.

[51] Int. Cl.$^3$ .............................................. C07C 47/052
[52] U.S. Cl. ....................................... 568/473; 568/471; 568/472; 568/474; 568/487; 568/489; 502/178; 502/348
[58] Field of Search ............... 568/473, 471, 472, 474, 568/487, 489; 252/461

[56] References Cited

U.S. PATENT DOCUMENTS

| | | | |
|---|---|---|---|
| 3,948,997 | 4/1976 | Howe et al. | 568/473 |
| 3,956,184 | 5/1976 | Kruglikov | 568/473 |
| 4,167,527 | 9/1979 | Nielsen | 568/473 |
| 4,358,623 | 11/1982 | Murphy | 568/472 |
| 4,359,587 | 11/1982 | Abdurakhmanov | 568/473 |
| 4,390,730 | 6/1983 | Gerberich | 568/473 |

*Primary Examiner*—Werren B. Lone
*Attorney, Agent, or Firm*—Linn Grim

[57] ABSTRACT

New catalysts comprising lead and silver on supports having relatively low surface areas and their use have been found to be useful in the oxidative dehydrogenation of methanol to formaldehyde at elevated temperatures.

21 Claims, No Drawings

FORMALDEHYDE PRODUCTION

This is a divisional of application Ser. No. 287,385, filed July 27, 1981.

FIELD OF THE INVENTION

This invention relates to new catalysts comprising lead and silver on inert support containing low surface areas and their improvements in their use for the production of formaldehyde by the oxidative dehydrogenation of methanol.

BACKGROUND OF THE INVENTION

Silver crystals in the form of granules, gauze, wire turnings, crystals, and the like have been used for many years to produce formaldehyde by the oxidative dehydrogenation of methanol. Silver crystals are especially suitable for this purpose since they are very selective and have little tendency to promote side reactions and the formation of by-products under reaction conditions which permit high overall yields. However, when using such crystals, the silver surface available for catalysis is relatively small compared to the remaining silver of the catalyst in the interior of the crystals which is not so available. Thus there has been a continuous effort to find a satisfactory catalyst wherein silver is deposited on an inert support for its more effective use in the production of formaldehyde from methanol.

Numerous prior art patents and publications describe silver on inert supports used as catalysts used in the production of formaldehyde from methanol. For example, U.S. Pat. No. 3,956,184, issued to Kruglikov et al on May 11, 1976, describes catalysts containing silver on supports such as silica gel, carborundum, corundum, pumice, diatomaceous earth, perlite and the like used for this purpose. Silver on an alumina support is shown in U.S. Pat. No. 3,959,383 issued to Northeimer on May 25, 1976. Catalysts comprising silver-gold alloys on various supports are described in U.S. Pat. No. 4,167,527 issued to Nielsen on Sept. 11, 1979.

Silver containing up to 10% of an oxide of barium, strontium and/or calcium and up to 8% of an oxide of indium on any of various supports such as silicon nitride, boron nitride, silicon carbide, silica and alumina are described as methanol oxidative dehydrogenation catayIsts in U.S. Pat. No. 4,045,369 issued to Cantiluppi on Aug. 30, 1977. Silver catalysts on support materials are described in U.S. Pat. No. 2,424,085 issued to Bergsteinsson et al on July 15, 1947. The support materials disclosed include elemental silicon, silicon carbide, or silicon-silicon carbide aggregates. These catalysts can be used in various processes such as oxidation, dehydrogenation, and the like. U.S. Pat. No. 3,948,997, issued Apr. 6, 1976 to Howe et al. describes a process for the vapor phase oxidation of $\alpha$, $\beta$-diols such as ethylene glycol to $\alpha$, $\beta$-diones such as glyoxal at elevated temperatures in the presence of a catalyst containing as essential constituents, one or more metals of Group Ib of the Periodic Table comprising copper, silver and gold, and one or more elements from Group IV a, comprising germanium, tin and lead, and Group V a, comprising nitrogen, phosphorus, arsenic, antimony and bismuth. The catalyst may be supported, if desired on an inorganic support material, for example, pumice and alumina. However, there is no specific disclosure in this patent of a lead-silver catalyst per se nor is there any suggestion that any of the catalysts disclosed generically or specifically, could be used for the oxidative dehydrogenation of methanol to formaldehyde.

Silver catalysts are also known for their use in the production of ethylene oxide from ethylene. U.S. Pat. No. 4,255,341 issued to Solomon on Mar. 10, 1981 describes ethylene oxidation catalysts including silver on supports such as $\alpha$-alumina and silicon carbide among other supports. U.S. Pat. No. 4,242,235 issued to Cogmon et al on Dec. 30, 1980 describes ethylene oxide catalysts of silver on refractory supports such as $\alpha$-alumina, silica-aluminas, silicon carbide, zirconia and graphite. However, none of these patents disclose or suggest supported lead-silver catalysts.

DETAILED DESCRIPTION OF THE INVENTION

A new catalyst comprising lead and silver on a support having a surface area below about 5 $m^2/g$ has been discovered which provides improvements in the production of formaldehyde by the oxidative dehydrogenation of methanol vapor at elevated temperatures.

The new catalysts of this invention can be prepared using any convenient method wherein the desired amount of lead and silver is deposited on low surface area support, i.e., one having a surface area below about 5 $m^2/g$, preferably below about 1.5 $m^2/g$. One technique for depositing the lead and silver on the support or carrier is to combine initially a water solution containing the desired amount of a water soluble heat decomposable silver salt such as silver acetate, silver nitrate and the like, with the desired amount of a water soluble heat decomposable lead salt such as lead acetate, lead nitrate, and the like.

The dissolved salts present in the solution contain lead and silver in the amounts desired in the final catalyst. In one method of preparation, the support is wetted with the entire aqueous lead and silver solution and the aqueous solvent removed by heating at 100° C. under vacuum. In another method, the lead and silver aqueous solution is added in increments.

The ratio of lead to silver in the supported catalyst can vary from about 0.005 to about 0.15 more preferably from about 0.012 to about 0.095 by weight. The silver may be present in an amount ranging from about 4 to about 20 weight percent preferably from about 10 to about 17 weight percent of the total catalyst, and the lead in an amount ranging from about 0.07 to about 1.50 weight percent, preferably from about 0.16 to about 1.45 weight percent of the total catalyst.

The support or carrier employed in the production of supported lead-silver catalysts in accordance with this invention comprise any of the solid supports having a surface area below about 5 $m^2/g$ heretofore employed in catalyst preparation. Suitable supports include for example: silicon carbide, $\alpha$-alumina, boron nitride, tungsten carbide, titania, zirconia, boron carbide and the like. The preferred supports used in the catalysts of this invention are silicon carbide and (alpha) $\alpha$-alumina having a surface area of less than 1.5 $m^2/g$.

The support or carrier particles used for the catalysts of this invention may be of any size forming the basis of catalysts which can be used conveniently for the oxidative dehydrogenation of methanol to formaldehyde, e.g., from about 4 to about 50 U.S. screen mesh size (i.e., particles which will pass through a 4 mesh screen but will be retained on a 50 mesh screen). The preferred particle sizes of the support are in the range of from about 14 to about 35 mesh. In some instances, catalysts containing a minor proportion of support particles larger than 4 mesh, i.e. up to 10 weight percent of the total support, can be tolerated in the methanol conversion but if the amount of large catalyst particles becomes excessive, the contact of methanol and oxygen with the catalyst will be significantly decreased resulting in lessened formaldehyde production. On the other hand, a small amount of support particles smaller than 50 mesh (again up to 10 weight percent of the total catalyst) can be used in the catalyst for the methanol reaction. However, if a significant amount of smaller particles are present, an undesirable increase in pressure drop across the catalyst bed may be observed.

The process of this invention can be carried out in any conventional single stage or multiple stage methanol oxidation reactor at elevated temperatures Individual reactors require facilities to hold a sufficient amount of oxidative dehydrogenation catalyst and to permit the methanol-oxygen mixture to pass over the catalyst to accomplish oxidative dehydrogenation. Downstream facilities to recover the formaldehyde product, normally in the aqueous solution, are also required.

In carrying out the process of this invention, a feed mix of methanol and an oxygen-containing stream, e.g., one containing about 5 mole percent to about 100 mole percent of oxygen such as pure oxygen, a mixture of oxygen and nitrogen, air or other oxygen source, is passed into a reactor containing a supported catalyst of this invention comprising lead and silver and reacted at a temperature in the range from about 500° C. to about 700° C., preferably about 550° C. to about 650° C. Diluents such as steam and nitrogen, if desired, can be added to the methanol-oxygen mixture in amounts ranging from about 0.1 to about 10 mole of diluent per mole methanol in feed, preferably about 0.75 to about 3 mole per mole methanol in feed. The mole ratio of oxygen to methanol in the feed can range from about 0.15 to about 0.8, preferably from about 0.2 to about 0.5. The space velocity of the feed entering the reactor will generally be maintained at from about 10 to about 150 reciprocal seconds, and preferably at from about 25 to about 80 reciprocal seconds.

Single stage operations, such as described above, although quite widely used to produce formaldehyde, suffer from the disadvantage that rather high amounts of unconverted methanol are contained in the product emerging from the catalyst bed. The presence of methanol in the exiting formaldehyde solution is undesirable since the methanol, generally, must be separated from the formaldehyde using expensive distillation facilities. However, the need for a separation step can be avoided by using a second oxidation stage or reaction. When carrying out a second oxidation, the effluent gases from the first stage reactor can be cooled, preferably below about 250° C., and mixed with an additional oxygen-containing stream, such as air. The effluent gas-oxygen mixture is then passed through a second stage catalytic oxidation dehydrogenation reactor containing sufficient catalyst to convert substantially all of the remaining unreacted methanol to formaldehyde. Temperatures in the range from about 550° C. to about 700° C., and preferably from about 600° C. to about 675° C., generally will be employed, while the space velocity of the gas in the second stage oxidation reactor generally will be maintained in the range of from about 10 to about 200 reciprocal seconds and preferably from about 30 to about 100 reciprocal seconds. Two stage oxidation processes for the conversion of methanol to formaldehyde are described in U.S. Pat. Nos. 2,462,413; 3,959,383; 3,987,107 and 4,076,754, among others.

When a two-stage process as described previously is employed, the supported catalyst of the present invention comprising lead and silver is utilized in the first stage oxidation dehydrogenation reaction stage and may also be utilized in the second stage. Alternatively, any other catalyst for the conversion of methanol to formaldehyde and preferably a silver-containing catalyst, can be used in the second stage oxidation stage.

The effluent gas emerging from the second stage may be passed through a cooler and then passed into the base of an absorber column. A stream of water may be introduced at the top of the absorber column in order to adjust the formaldehyde concentration in the aqueous formaldehyde product which is removed from the bottom of the column. The non-condensable gases entering the absorber are vented at the top of the column to an incinerator or to the atmosphere.

The following examples further illustrate the invention:

EXAMPLES 1–50

An amount of silicon carbide carrier was wetted with the salt solution containing the total amount of metallic elements desired in the final catalyst. The aqueous solvent was removed by heating at 100° C. under vacuum.

As an illustration, to prepare a silver-lead on silicon carbide catalyst containing 13.0 weight percent metals with a lead to silver ratio of 0.048 by weight, silver nitrate (2.25 grams) and lead nitrate (0.11 gram) were dissolved in demineralized water (total solution volume of 5.2 ml). This solution was poured onto 10 grams of the support. Water was removed by heating at 100° C. under vacuum. When bismuth nitrate was used in combination with lead and/or silver nitrate, a small amount of nitric acid was employed to aid in dissolving the bismuth nitrate. The silver on silicon carbide catalyst was prepared in the same manner as the catalyst comprising lead and silver, but without utilizing any lead salt.

The methanol oxidation unit used for these examples was an insulated, cylindrical reactor made of 316 stainless steel which is 7 inches long and has an internal diameter of ⅜ inch. In each run, the catalyst was employed in a bed 1.0 inch deep. A thermocouple inserted into the catalyst bed was used to measure the reaction temperature. Air [7605 cc (STP)/min] was sparged into a heated vessel of liquid methanol. The gas leaving the vaporizer had an air to methanol ratio as indicated in Table I. This vapor stream was mixed with a flow of pure nitrogen (1949 cc/min), heated to 125° C. to avoid condensation, and fed to the methanol oxidation unit described above. Reaction was initiated by heating the catalyst bed with an electric resistance winding which is on the external surface of the reactor. As soon as the methanol conversion reaction was initiated, as indicated by a sudden rise in temperature to 450° C. or above, the timing of the run was begun. The conversions of methanol obtained were at levels ranging from 60.1 percent to 75.7 percent and were controlled by keeping the air and thus the oxygen in the feed stream constant and varying the oxygen-methanol ratio by controlling the methanol in the stream, with higher oxygen-methanol ratios yielding higher methanol conversions. Once the reaction, which is exothermic, was initiated, the temperature was permitted to reach its own level, with no external heat being added to the reaction and no heat being deliberately absorbed by heat exchangers while the reaction is continuing, although an undetermined amount of heat may of course have escaped into the surroundings through the reactor walls. The product stream was analyzed by gas chromatography for mole percent nitrogen, oxygen, methanol, carbon monoxide, carbon dioxide, hydrogen, and methyl formate. The conditions of the reaction were:

catalyst temperature-529°-659° C.
reaction pressure-5.8 psig
oxygen conversion-99.5 percent
space velocity-26 sec$^{-1}$ The silicon carbide carrier was produced from 3/16 inch spheres; in some examples these spheres were used as the carrier without modification. In other examples utilizing smaller catalyst particles, the 3/16 inch spheres were crushed and sieved to achieve the desired screen mesh size (U.S. screen size). The 3/16 inch silicon carbide spheres have a surface area of less than 1 m$^2$/g. The silicon carbide carriers used contain approximately 60-78% silicon carbide, 4-11% aluminum oxide (Al$_2$O$_3$), and 14-26% SiO$_2$, and it was found that any differences in carrier composition within these ranges did not affect the results obtained. Table I sets out the results of methanol oxidative dehydrogenation to formaldehyde using varying amounts of silver and lead-silver on various silicon carbide carriers of varying sizes. The table indicates catalyst temperatures used in the reaction, length of run, conversions of methanol to total products, and the efficiencies of converted methanol to carbon dioxide (CO$_2$), carbon monoxide (CO), methyl formate (MeFo) and formaldehyde (HCHO).

TABLE I

SILICON CARBIDE SUPPORTED CATALYSTS

| Example | Support Mesh or Size | Carrier | Ag Wt % | Pb Wt % | Bi Wt % | Air/Methanol Mole Ratio | Length of Runs, Hours | Temp °C. | Conv. % | HCHO % | CO$_2$ % | CO % | MeFo % |
|---|---|---|---|---|---|---|---|---|---|---|---|---|---|
| 1 | 3/16" | 1 | 9.1 | — | — | 1.13 | 15 | 561 | 61.5 | 86.1 | 9.8 | 1.8 | 2.4 |
| 2 | 3/16" | 1 | 16.1 | — | — | 1.15 | 7 | 548 | 60.2 | 83.4 | 11.0 | 3.4 | 2.2 |
| 3 | 14-28 | 1 | 9.1 | — | — | 1.28 | 38 | 640 | 60.1 | 87.2 | 9.9 | 2.7 | 0.2 |
| 4 | 14-28 | 1 | 9.1 | — | — | 1.15 | 18 | 580 | 67.3 | 91.5 | 6.6 | 0.2 | 1.1 |
| 5 | 14-28 | 1 | 9.1 | — | — | 1.23 | 42 | 596 | 71.7 | 91.3 | 7.1 | 0.6 | 1.0 |
| 6 | 14-28 | 1 | 13 | — | — | 1.22 | 28 | 566 | 72.3 | 91.6 | 6.8 | 0.5 | 1.1 |
| 7 | 14-28 | 1 | 13 | — | — | 1.09 | 34 | 553 | 66.1 | 92.4 | 6.2 | 0 | 1.4 |
| 8 | 14-28 | 1 | 13.0 | — | — | 1.15 | 28 | 577 | 67.6 | 90.9 | 7.24 | 0 | 1.87 |
| 9 | 14-28 | 1 | 13.0 | — | — | 1.22 | 40 | 595 | 72.3 | 90.4 | 7.65 | 0.33 | 1.60 |
| 10 | 4-8 | 2 | 4.6 | 1.85 | 0.93 | 1.25 | 13 | 625 | 52.7 | 46.0 | 8.1 | 45.2 | 0.6 |
| 11 | 4-8 | 2 | 16.3 | 1.63 | .41 | 1.30 | 15 | 632 | 62.5 | 82.4 | 8.23 | 8.59 | 0.78 |
| 12 | 4-8 | 2 | 4.8 | — | — | 1.20 | 12 | 549 | 66.9 | 79.5 | 7.6 | 11.8 | 1.0 |
| 13 | 4-8 | 2 | 12.7 | 0.35 | — | 1.32 | 19 | 620 | 71.6 | 88.8 | 7.5 | 2.9 | 0.8 |
| 14 | 4-8 | 2 | 12.7 | 0.35 | — | 1.15 | 39 | 557 | 66.4 | 90.2 | 6.8 | 0.9 | 2.1 |
| 15 | 14-28 | 1 | 12.4 | 0.61 | — | 1.27 | 39 | 530 | 74.1 | 92.9 | 5.9 | 0.0 | 1.1 |
| 16 | 14-28 | 1 | 12.4 | 0.61 | — | 1.09 | 62 | 529 | 65.8 | 93.5 | 5.0 | 0.0 | 1.4 |
| 17 | 14-28 | 1 | 12.4 | 0.61 | — | 1.22 | 75 | 543 | 72.3 | 92.6 | 5.9 | 0.3 | 1.2 |
| 18 | 14-28 | 1 | 12.4 | 0.61 | — | 1.27 | 42 | 598 | 71.4 | 92.4 | 6.7 | 0.0 | 0.9 |
| 19 | 14-28 | 2 | 12.4 | 0.61 | — | 1.17 | 17 | 580 | 66.3 | 92.2 | 6.3 | 0.0 | 1.5 |
| 20 | 14-28 | 2 | 12.4 | 0.61 | — | 1.26 | 33 | 601 | 72.2 | 92.0 | 6.9 | 0.0 | 1.1 |
| 21 | 14-28 | 3 | 12.4 | 0.61 | — | 1.19 | 18 | 610 | 65.7 | 92.7 | 6.0 | 0.0 | 1.3 |
| 22 | 14-28 | 3 | 12.4 | 0.61 | — | 1.28 | 30 | 623 | 72.2 | 92.4 | 6.6 | 0.0 | 1.0 |
| 23 | 14-28 | 1 | 15.17 | 1.45 | — | 1.24 | 21 | 659 | 64.4 | 92.5 | 6.9 | 0.0 | 0.6 |
| 24 | 14-28 | 1 | 15.17 | 1.45 | — | 1.33 | 39 | 636 | 72.5 | 91.5 | 7.6 | 0.0 | 0.9 |
| 25 | 14-28 | 1 | 12.7 | 0.30 | — | 1.24 | 19 | 574 | 72.2 | 93.3 | 5.7 | 0.0 | 1.0 |
| 26 | 14-28 | 1 | 12.7 | 0.30 | — | 1.12 | 28 | 558 | 67.5 | 93.5 | 5.1 | 0.0 | 1.4 |
| 27 | 14-28 | 1 | 12.7 | 0.30 | — | 1.19 | 42 | 562 | 71.3 | 93.0 | 5.6 | 0.0 | 1.4 |
| 28 | 28-35 | 1 | 12.9 | 0.16 | — | 1.10 | 18 | 566 | 66.1 | 93.5 | 5.1 | 0.0 | 1.4 |
| 29 | 28-35 | 1 | 12.9 | 0.16 | — | 1.21 | 27 | 591 | 72.4 | 93.1 | 5.8 | 0.0 | 1.1 |
| 30(b) | 14-28 | 1 | 12.4 | .61 | — | 1.26 | 41 | 604 | 72.4 | 92.0 | 6.24 | 0 | 1.74 |
| 31(b) | 14-28 | 1 | 12.4 | .61 | — | 1.34 | 50 | 608 | 75.7 | 91.8 | 6.61 | 0 | 1.56 |
| 32 | 14-28 | 1 | 12.4 | .61 | — | 1.16 | 12 | 561 | 59.4 | 94.4 | 4.86 | 0 | 0.73 |
| 33 | 14-28 | 1 | 12.4 | .61 | — | 1.22 | 32 | 608 | 65.2 | 94.1 | 5.15 | 0 | 0.76 |
| 34 | 14-28 | 1 | 12.4 | .61 | — | 1.26 | 49 | 601 | 71.7 | 93.5 | 5.56 | 0 | 0.91 |
| 35 | 14-28 | 1 | 12.4 | .61 | — | 1.22 | 14 | 624 | 66.4 | 93.8 | 5.6 | 0 | 0.7 |
| 36 | 14-18 | 1 | 12.4 | .61 | — | 1.29 | 37 | 622 | 74.9 | 92.9 | 6.2 | 0 | 0.9 |
| 37(a) | 14-28 | 1 | 12.4 | .61 | — | 1.17 | 15 | 588 | 65.5 | 93.4 | 5.27 | 0. | 1.34 |
| 38(a) | 14-28 | 1 | 12.4 | .61 | — | 1.26 | 43 | 607 | 71.4 | 93.5 | 5.51 | 0 | 1.02 |
| 39 | 14-28 | 1 | 4.7 | .66 | .09 | 1.22 | 23 | 632 | 66.5 | 91.7 | 5.31 | 2.01 | 0.98 |
| 40 | 14-28 | 1 | 4.7 | .66 | .09 | 1.28 | 47 | 619 | 70.3 | 91.6 | 5.58 | 1.75 | 1.09 |
| 41 | 14-28 | 1 | 16.3 | 1.2 | .81 | 1.25 | 17 | 644 | 64.3 | 93.1 | 5.20 | 1.21 | 0.48 |
| 42 | 14-28 | 1 | 16.3 | 1.2 | .81 | 1.33 | 38 | 651 | 69.8 | 93.3 | 5.52 | 0.68 | 0.53 |
| 43 | 14-28 | 1 | 13.0 | .05 | — | 1.25 | 23 | 590 | 72.7 | 91.3 | 7.09 | 0 | 1.64 |
| 44 | 14-28 | 1 | 13.0 | .05 | — | 1.12 | 42 | 561 | 65.7 | 91.2 | 6.53 | 0 | 2.26 |
| 45 | 14-28 | 1 | 12.7 | — | .30 | 1.28 | 18 | 624 | 63.1 | 90.9 | 6.6 | 1.7 | 0.8 |
| 46 | 14-28 | 1 | 12.3 | .43 | .43 | 1.25 | 28 | 604 | 65.5 | 92.5 | 5.8 | 0.4 | 1.3 |
| 47 | 14-28 | 1 | 12.3 | .43 | .43 | 1.27 | 47 | 632 | 67.7 | 93.5 | 5.6 | 0.0 | 0.9 |
| 48 | 14-28 | 1 | 12.3 | .43 | .43 | 1.29 | 63 | 608 | 69.7 | 92.7 | 6.0 | 0.0 | 1.3 |
| 49 | 14-28 | 1 | 12.6 | .43 | .04 | 1.31 | 34 | 616 | 72.2 | 92.7 | 6.2 | 0.0 | 1.1 |
| 50 | 14-28 | 1 | 15.9 | — | .75 | 1.29 | 20 | 628 | 64.5 | 90.6 | 6.2 | 2.5 | 0.7 |

Carrier Major Composition
(1) SiO$_2$—16.5%, Al$_2$O$_3$—5.86%, SiC—75.9% - Surface area 0.27 m$^2$/g square meters per gram
(2) SiO$_2$—14.5%, Al$_2$O$_3$—4.38%, SiC—77.78% - Surface area 0.20 m$^2$/g square meters per gram
(3) SiO$_2$—26.37%, Al$_2$O$_3$—11.42%, SiC—59.1% - Surface area 0.31 m$^2$/g square meters per gram
(a) Catalyst calcined in air at 585° C. for 20 hours before reaction
(b) Catalyst calcined in air at 260° C. for 24 hours, then at 650° C. for 24 hours before reaction Certain results from Table I of the oxidative dehydrogenation of methanol over catalysts containing lead and silver on silicon carbide are compared in Table II below with those obtained with catalysts containing silver only on silicon carbide at the same methanol conversion levels of ~72% and ~66-67%.

TABLE II
COMPARISON OF Ag/SILICON CARBIDE WITH Ag—Pb/SILICON CARBIDE

| Example | Carrier Size Mesh | Ag % | % Pb | % Methanol Conversion | % Formaldehyde Efficiency |
|---|---|---|---|---|---|
| ~72% METHANOL CONVERSION | | | | | |
| 6 | 14-28 | 13 | 0 | 72.3 | 91.6 |
| 9 | 14-28 | 13 | 0 | 72.3 | 90.4 |
| 17 | 14-28 | 12.4 | 0.61 | 72.3 | 92.6 |
| 18 | 14-28 | 12.4 | 0.61 | 71.4 | 92.4 |
| 20 | 14-28 | 12.4 | 0.61 | 72.2 | 92.0 |
| 22 | 14-28 | 12.4 | 0.61 | 72.2 | 92.4 |
| 25 | 14-28 | 12.7 | 0.30 | 72.2 | 93.3 |
| 27 | 14-28 | 12.7 | 0.30 | 71.3 | 93.0 |
| 29 | 28-35 | 12.9 | 0.16 | 72.4 | 93.1 |
| 30 | 14-28 | 12.4 | 0.61 | 72.4 | 92.0 |
| 34 | 14-28 | 12.4 | 0.61 | 71.7 | 93.5 |
| 38 | 14-28 | 12.4 | 0.61 | 71.4 | 93.5 |
| 43 | 14-28 | 13.0 | 0.05 | 72.7 | 91.3 |
| ~66-67% METHANOL CONVERSION | | | | | |
| 7 | 14-28 | 13 | 0 | 66.1 | 92.4 |
| 8 | 14-28 | 13 | 0 | 67.6 | 90.9 |
| 16 | 14-28 | 12.4 | 0.61 | 65.8 | 93.5 |
| 19 | 14-28 | 12.4 | 0.61 | 66.3 | 92.2 |
| 21 | 14-28 | 12.4 | 0.61 | 65.7 | 92.7 |
| 26 | 14-28 | 12.7 | 0.30 | 67.5 | 93.5 |
| 28 | 28-35 | 12.9 | 0.16 | 66.1 | 93.5 |
| 33 | 14-28 | 12.4 | 0.61 | 65.2 | 94.1 |
| 35 | 14-28 | 12.4 | 0.61 | 66.4 | 93.8 |
| 37 | 14-28 | 12.4 | 0.61 | 65.5 | 93.4 |
| 44 | 14-28 | 13.0 | 0.05 | 65.7 | 91.2 |

Although at the ~72% conversion level, Example 6 employing only silver on the silicon carbide support yields a formaldehyde efficiency of 91.6%, almost as good as that obtained in Example 30, viz. 92.0% which utilized a catalyst containing silver and 0.61% of lead, and at the ~66-67% conversion level, Example 7 employing a lead-free supported catalyst yielded a formaldehyde efficiency comparable to that of Examples 19 and 21 which utilized a catalyst containing 0.61% of lead in addition to silver, the results shown in this table as a whole indicate that the supported catalysts comprising silver and lead in most cases yield better results in terms of formaldehyde yield and methanol utilization than are obtained with lead-free supported silver catalysts. It should also be noted that Example 43 at the 72% conversion level and Example 44 at the ~66-67% conversion level both of which employed a catalyst containing 0.05% lead, yielded lower efficiencies than the other examples utilizing higher amounts of lead in the catalyst. This indicates that the lead content must be increased above 0.05 weight percent of the catalyst or 500 parts per million to obtain the improved results for formaldehyde efficiencies.

The results shown in Table I also indicate that bismuth-silver without lead on silicon carbide (Examples 45 and 50) did not provide the improved formaldehyde efficiencies over the use of supported silver catalysts containing no bismuth. The presence of a small amount of bismuth in combination with lead and silver on a silicon carbide support (Examples 39-42) does not raise the efficiencies of formaldehyde from methanol over those obtained with supported lead and silver catalysts. The catalyst of Example 10 using 1.85 weight percent lead in combination with 4.6 weight percent silver and bismuth at 0.93 weight percent on a silicon carbide support (4-8 mesh), provides an unsatisfactory formaldehyde efficiency of 46% at 52.7% methanol conversion level indicating that the lead content was too high.

As brought out previously, the recorded temperatures are those resulting after the initiation of reaction without any external temperature control. Within the range reported in the examples, temperature of reaction is not believed to affect formaldehyde efficiency at a set methanol conversion level.

The varying values of length of run reported in these and the other examples disclosed herein are also believed not to affect the results in terms of formaldehyde efficiency since these values are considerably below the minimum catalyst age at which the activity of the catalyst is adversely affected.

EXAMPLES 51-68B

Various sizes of a carrier identified as Celite I which has a composition of 75% SiO$_2$ and 10% Al$_2$O$_3$ and a surface area of 19 m$^2$/g, were used as the carrier for the catalysts employed in these examples. The catalysts contained varying amounts of silver alone or lead and silver and were used in the methanol oxidation to formaldehyde in the same unit under the same conditions except for slight variations in temperature, as used for Examples 1-50 at a catalyst depth of 1.0 inch. Table III sets out the results obtained using the same symbols as used in Table I.

TABLE III
75% SiO$_2$ 10% Al$_2$O$_3$ SUPPORTED CATALYSTS

| Example | Support Mesh Size or mm | Ag Wt % | Other Metals % | Air/Methanol Mole Ratio | Length of Runs Hours | Temp °C. | Methanol Conv. | HCHO % | CO$_2$ % | CO % | MeFo % |
|---|---|---|---|---|---|---|---|---|---|---|---|
| 51 | ⅛" | 9.1 | — | 1.14 | 21 | 596 | 60.4 | 86.9 | 9.3 | 2.2 | 1.6 |
| 52 | ⅛" | 9.1 | — | 1.06 | 27 | 581 | 56.7 | 87.6 | 9.0 | 1.3 | 2.1 |
| 53 | 6-10 | 16.7 | — | 1.13 | 6 | 607 | 61.0 | 89.4 | 7.7 | 2.2 | 0.7 |
| 54 | 6-10 | 16.7 | — | 1.21 | 20 | 628 | 63.6 | 89.0 | 7.6 | 2.7 | 0.5 |
| 55 | 6-10 | 16.7 | — | 1.21 | 35 | 603 | 64.8 | 89.6 | 7.9 | 1.8 | 0.8 |
| 56 | ⅛" | 16.7 | — | 1.14 | 10 | 571 | 58.7 | 81.0 | 8.6 | 8.7 | 1.6 |
| 57 | 8-14 | 16.7 | — | 1.14 | 9 | 568 | 63.4 | 89.8 | 8.3 | 0.9 | 1.0 |
| 58 | 14-28 | 16.7 | — | 1.16 | 13 | 578 | 64.6 | 90.1 | 7.9 | 1.2 | 0.8 |
| 59 | 14-28 | 16.7 | — | 1.18 | 38 | 597 | 63.5 | 90.9 | 7.0 | 1.9 | 0.2 |
| 60 | 14-28 | 9.1 | — | 1.19 | 12 | 606 | 64.4 | 90.2 | 7.6 | 1.9 | 0.3 |
| 61 | 14-28 | 9.1 | — | 1.18 | 24 | 583 | 63.8 | 89.5 | 7.6 | 1.7 | 1.2 |
| 62 | 14-28 | 28.6 | — | 1.15 | 16 | 571 | 65.7 | 90.2 | 8.0 | 1.0 | 0.9 |
| 63 | 14-28 | 28.6 | — | 1.15 | 26 | 590 | 66.8 | 90.3 | 7.7 | 1.2 | 0.7 |
| 64 | 14-28 | 28.6 | — | 1.30 | 40 | 601 | 73.2 | 88.9 | 8.8 | 1.7 | 0.5 |
| 65 | 14-28 | 4.8 | — | 1.25 | 8 | 638 | 63.6 | 89.2 | 7.6 | 3.2 | 0.0 |
| 66 | 14-28 | 13.0 | — | 1.15 | 16 | 615 | 64.0 | 90.9 | 7.4 | 0.9 | 0.8 |

TABLE III-continued

| | 75% SiO$_2$ 10% Al$_2$O$_3$ SUPPORTED CATALYSTS | | | | | | | | | | |
|---|---|---|---|---|---|---|---|---|---|---|---|
| Example | Support Mesh Size or mm | Ag Wt % | Other Metals % | Air/Methanol Mole Ratio | Length of Runs Hours | Temp °C. | Methanol Conv. | HCHO % | CO$_2$ % | CO % | MeFo % |
| 67 | 14–28 | 12.4 | 0.6(Pb) | 1.27 | 23 | 667 | 62.3 | 91.0 | 7.6 | 0.6 | 0.8 |
| 68 | 14–28 | 12.9 | 0.17(Pb) | 1.22 | 17 | 558 | 66.6 | 92.7 | 5.7 | 0.9 | 0.8 |
| 68A | 14–28 | 12.9 | 0.17(Pb) | 1.20 | 20 | 533 | 66.4 | 92.3 | 5.9 | 0.8 | 0.9 |
| 68B | 14–28 | 12.9 | 0.17(Pb) | 1.31 | 44 | 587 | 71.7 | 91.4 | 6.5 | 1.5 | 0.6 |

It should be noted that in Table III, Examples 68–68B describing catalysts comprising 0.17 weight percent lead and 12.9 weight percent silver on SiO$_2$-Al$_2$O$_3$ supports, better results, in regard to formaldehyde efficiencies, were obtained compared to Example 66 using 13 weight percent silver on SiO$_2$-Al$_2$O$_3$ support. Example 67, describing the use of 0.6 weight percent lead and 12.4 weight percent silver on SiO$_2$-Al$_2$O$_3$ support, resulted in exceptionally high temperature of 667° C. to yield a formaldehyde efficiency of 91 percent at 62.3 percent methanol conversion. This relatively high temperature appears to be an anomaly in view of the lower temperatures reached in obtaining the formaldehyde efficiencies indicated with the catalysts of the other examples in Table III of silver alone and silver and lead on SiO$_2$-Al$_2$O$_3$ support. Furthermore, the result of Example 67 is not consistent with the results obtained using other catalysts comprising lead and silver on SiO$_2$-Al$_2$O$_3$ supports since the result is not significantly better than the results of Example 66 (13 weight percent silver on SiO$_2$-Al$_2$O$_3$).

EXAMPLES 69–75

Using an α-alumina carrier (87% Al$_2$O$_3$ and 11.7% SiO$_2$) having a surface area of less than 1.0 m$^2$/g as a support for silver and the combination of lead and silver, the catalysts were prepared using the procedure set forth in Examples 1–50. The methanol oxidation unit and conditions employed were the same as those used in Examples 1–50 except for slight variations in temperature. Table IV sets out the results using the same symbols as were used for Table I.

dehydrogenation of methanol to formaldehyde utilizing a catalyst comprising silver on a support, and methanol conversions of 60 to 75% the employment of a small amount of lead with the silver makes it possible to increase the formaldehyde efficiency at a set methanol conversion by at least 1%. This is a significant economic advantage in terms of the increased formaldehyde yield obtained.

What is claimed is:

1. In a process for the production of formaldehyde by oxidative dehydrogenation of methanol vapor with oxygen gas at elevated temperatures from about 500° C. to about 700° C., the improvement comprising passing a vapor mixture comprising methanol and an oxygen-containing gas over a catalyst comprising lead and silver on a support having a surface area below about 5 m$^2$/g, the weight ratio of lead to silver ranging from about 0.005 to about 0.15.

2. The process of claim 1 wherein the weight ratio of lead to silver in the catalyst ranges from about 0.016 to about 0.095.

3. The process of claim 1 wherein the amount of silver ranges from about 4 to about 20 weight percent of the total catalyst and the amount of lead ranges from about 0.07 to about 1.50 weight percent of the total catalyst.

4. The process of claim 1 wherein the amount of silver ranges from about 10 to about 17 weight percent of the total catalyst and the amount of lead ranges from about 0.16 to about 1.45 weight percent of the total catalyst.

5. The process of claim 1 wherein said support has a

TABLE IV

| | α-ALUMINA SUPPORTED CATALYSTS | | | | | | | | | | |
|---|---|---|---|---|---|---|---|---|---|---|---|
| | Support | | | Air/Methanol Mole | Length of Runs | Temp | Methanol | Efficiencies | | | |
| Example | Mesh Size or Inches | Ag Wt % | Pb Wt % | Ratio | Hours | °C. | Conv. % | HCHO % | CO$_2$ % | CO % | MeFo % |
| 69 | 3/16" | 9.1 | — | 1.16 | 16 | 563 | 63 | 85.0 | 11.1 | 1.8 | 2.0 |
| 70 | 3/16" | 9.1 | — | 1.15 | 6 | 586 | 62 | 84.8 | 10.5 | 3.1 | 1.7 |
| 71 | 14–28 | 13 | — | 1.20 | 7 | 570 | 72.2 | 90.3 | 7.89 | 0 | 1.8 |
| 72 | 14–28 | 13 | — | 1.28 | 20 | 587 | 76.8 | 90.2 | 8.3 | 0 | 1.5 |
| 73 | 14–28 | 13 | — | 1.07 | 27 | 571 | 66.0 | 90.6 | 7.01 | 0.4 | 1.9 |
| 74 | 14–28 | 12.6 | 0.43 | 1.17 | 19 | 562 | 67.1 | 92.4 | 5.9 | 0 | 1.67 |
| 75 | 14–28 | 12.6 | 0.43 | 1.25 | 44 | 583 | 72 | 92.1 | 6.3 | 0 | 1.63 |

The results of Table IV indicate that the catalysts comprising lead and silver on α-alumina (14–28 mesh) provided improved results compared to the catalysts of silver alone on α-alumina (14–28 mesh) in the oxidative dehydrogenation of methanol to formaldehyde. Thus, the lead-silver catalysts of Examples 74–75 yielded formaldehyde efficiencies of 92.1–92.4 percent at methanol conversions of 67.1–72 percent while the lead-free silver catalysts of Examples 71–73 provided lower formaldehyde efficiencies of 90.2–90.6 at methanol conversions of 66–76.8 percent.

Based on the results shown in the tables, it can be concluded that in a commercial unit for the oxidative surface area below about 1.5 m$^2$/g.

6. The process of claim 2 wherein said support has a surface area below about 1.5 m$^2$/g.

7. The process of claim 6 wherein the particle size of said support is from about 14 to about 35 mesh U.S. screen size.

8. The process of claim 6 wherein said support is silicon carbide.

9. The process of claim 7 wherein said support is silicon carbide.

10. The process of claim 6 wherein said support is α-alumina.

11. The process of claim 7 wherein said support is α-alumina.

12. In a two-stage process for the production of formaldehyde by oxidative dehydrogenation of methanol vapor with an oxygen-containing gas at elevated temperatures from about 500° C. to about 700° C., the improvement comprising passing a vapor mixture of methanol and an oxygen-containing gas in the first stage over a catalyst comprising lead and silver on a support having a surface area below about 5 m²/g, the weight ratio of lead to silver on said support ranging from about 0.005 to about 0.15; and passing the effluent gases from said first stage and additional oxygen-containing gas into a second stage over a silver containing catalyst.

13. The process of claim 12 wherein the weight ratio of lead to silver in said catalyst in said first stage ranges from about 0.016 to about 0.095.

14. The process of claim 12 wherein said catalyst in said first stage contains silver in the range of from about 4 to about 20 weight percent of the total catalyst and lead in the range of from about 0.07 to about 1.50 weight percent of the total catalyst.

15. The process of claim 13 wherein said support of said first stage catalyst has a surface area below about 1.5 m²/g.

16. The process of claim 14 wherein said support of said first stage catalyst is silicon carbide having a particle size in the range from about 14 to about 35 mesh U.S. screen size.

17. The process of claim 14 wherein said support of said first stage catalyst is α-alumina having a particle size in the range from about 14 to about 35 mesh U.S. screen size.

18. The process of claim 16 wherein the second stage catalyst comprises silver crystals.

19. The process of claim 17 wherein the second stage catalyst comprises silver crystals.

20. The process of claim 12 wherein the first and second stage catalysts comprise lead and silver on a silicon carbide support wherein the amount of silver ranges from about 10 to about 17 weight percent of the total catalyst; the amount of lead ranges from about 0.16 to about 1.45 weight percent of the total catalyst; the particle size of said silicon carbide support ranges from about 14 to about 35 mesh U.S. screen size and the weight ratio of lead to silver ranges from about 0.016 to about 0.095.

21. The process of claim 12 wherein the first and second stage catalysts comprise lead and silver on an α-alumina support wherein the amount of silver ranges from about 10 to about 17 weight percent of the total catalyst; the amount of lead ranges from about 0.16 to about 1.45 weight percent of the total catalyst; the particle size of said α-alumina support ranges from about 14 to about 35 mesh U.S. screen size; and the weight ratio of lead to silver ranges from about 0.016 to about 0.095.

* * * * *